United States Patent [19]

Bolton et al.

[11] Patent Number: 4,970,149
[45] Date of Patent: Nov. 13, 1990

[54] CLASS II RESTRICTION ENDONUCLEASE KSP632I, A PROCESS FOR OBTAINING IT AND THE USE THEREOF

[75] Inventors: Bryan J. Bolton, Winterslow, England; Michael Jarsch, Munich, Fed. Rep. of Germany; Gudrun Schmitz, Bernried, Fed. Rep. of Germany; Christoph Kessler, Munich, Fed. Rep. of Germany

[73] Assignee: Boehringer Mannheim GmbH, Mannheim, Fed. Rep. of Germany

[21] Appl. No.: 241,013

[22] Filed: Sep. 2, 1988

[30] Foreign Application Priority Data

Sep. 9, 1987 [DE] Fed. Rep. of Germany ....... 3730247
Aug. 3, 1988 [DE] Fed. Rep. of Germany ....... 3826389

[51] Int. Cl.$^5$ .......................... C12P 19/34; C12N 9/22
[52] U.S. Cl. ........................................ 435/91; 435/199
[58] Field of Search ................................. 435/199, 91

[56] References Cited

PUBLICATIONS

Bolton, B. J., et al, (1988) Gene 66(1) 31–43,
Polisson, C., et al. (1988) Nuc. Acids Res. 16(20) 9872.

Primary Examiner—Elizabeth C. Weimar
Assistant Examiner—Charles L. Patterson, Jr.
Attorney, Agent, or Firm—Felfe & Lynch

[57] ABSTRACT

The present invention provides a restriction endonuclease, characterized by the recognition sequence:

5'-CTCTTCN ↓ NNN-N-3'

3'-GAGAAGN-NNN ↑ N-5' and the cleavage position defined by the arrows. The present invention also provides a process for obtaining this new restriction endonuclease and a method for using the endonuclease.

7 Claims, No Drawings

CLASS II RESTRICTION ENDONUCLEASE KSP632I, A PROCESS FOR OBTAINING IT AND THE USE THEREOF

The present invention is concerned with a new Class II restriction endonuclease Ksp632I, with a process for obtaining it and with the use thereof Class II restriction endonucleases are endodeoxyribonucleases, which are able to recognize and cleave certain DNA nucleotide sequence. One phosphodiester bridge is hydrolyzed in each polynucleotide chain of the target sequence. Class II restriction endonucleases are valuable for the analyses of DNA molecules.

Specific Class II restriction endonucleases are admittedly already known for numerous recognition sequences, but there is still a need for additional Class II restriction endonucleases which are specific for recognition sequence where restriction endonucleases have not been recognized.

Therefore it is an object of the present invention to provide a new restriction endonuclease, which recognizes and cleaves a sequence which hitherto has not been recognized by any such enzyme.

Thus, according to the present invention, there is provided a restriction endonuclease, which is characterized by the palindromic recognition sequence:

5'-CTCTTCN ↓ NNN-N-3'

3'-GAGAAGN-NNN ↑ N-5' and the cleavage position defined by the arrows. The new Class II restriction endonuclease according to the present invention, referred to hereafter as Ksp632I, has an average temperature optimum of 37° C. and a pH optimum between pH 7.2 and pH 8.0 at a concentration of a monovalent cation at 70 mmol/l potassium acetate Further preferred optimum parameters are 10 mmol/l magnesium acetate and 0.5 mmol/l dithiothreitol.

The recognition sequence can be ascertained by complete digest of the DNA's of SV40 and adeno 2, the phages λ, and φX174, the phage derivative M13mp8 and the plasmids pBR322 and pBR328. The DNA's were digested with Ksp632I.

Table 1 shows a comparison between the experimental determined recognition specificity and a computer calculated recognition specificity for an enzyme, which recognizes the sequence CTCTTC.

The position of cleavage in the recognition sequence of the enzyme can be ascertained as follows:

The plasmid pUC18 (Gene 33 (1985) 103-109) is linearized with EcoRI or SacI. The EcoRI fragment is labeled on the 5'end with T4-polynucleotide kinase by use of [γ³ ²P]-ATP. The 3'end of the SacI fragment is also labeled by use of terminal transferase and [α³ ²P]-ddATP (i.e., dedeoxy ATP) with ³ ²P.

After an additional digest the fragments, which are 5' labeled at the EcoRI end or 3' labeled at the SacI end, were isolated by agarose gel electrophoresis and purified from the gel.

An aliquot of these fragments is cleaved with Ksp632I and cleaved chemically simultaneously for sequencing (Methods in Enzymology 65, (1980), 499-560). The analysis of the fragments is done by sequence gel electrophoresis (5% polyacrylamide, 8 mol/l urea) and subsequent autoradiography. The interpretation of the results followed Methods in Enzymology 65, (1980), 391-401. It is found that Ksp632I cleaves between position 296/297 and 690/691, respectively of the sequence of the vector pUC18 with the specificity as follows:

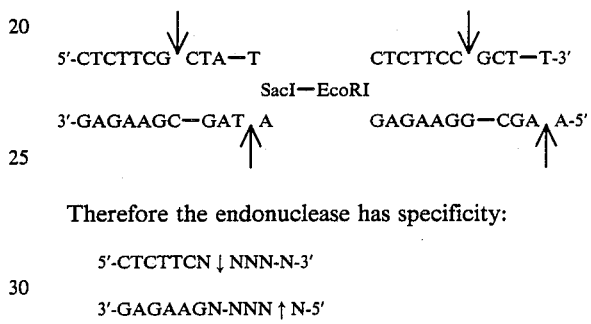

Therefore the endonuclease has specificity:

5'-CTCTTCN ↓ NNN-N-3'

3'-GAGAAGN-NNN ↑ N-5'

The experimentally found number of cleavage sites is identical with the number of cleavage sites obtained by computer analysis with the different DNA's for the sequence CTCTTC. (Table 1). In addition these data were compared with the data from the tables set forth in Gene 10: 357-370 (1980). Double digest of φX174 DNA with HgiAI and Ksp632I as well as of SV40 DNA with AvaII and Ksp632I confirm that the specificity is CTCTTC.

According to the present invention Ksp632I is obtained by growing Kluyvera species 632 (DSM 4196) and recovering the enzymes from the cells. For the recovery, there can be used the conventional biochemical purification methods, whereby in each of the fractions obtained the presence of the enzyme can be demonstrated on the basis of the cleavage of recognition sequence. As substrate there can be used for example adenovirus 2 DNA. The DNA of the fragments obtained are separated electrophoretically in agarose gels in the buffer systems conventional for fragment separation in the presence of ethidium bromide.

TABLE 1

| DNA | Number of experimental found cleavage sites | Number of computer-calculated cleavage sites | Experimental found length of fragments | Computer-calculated length of fragments | Computer-calculated cleavage sites |
| --- | --- | --- | --- | --- | --- |
| SV40 | 1 | 1 | 5250 | 5243 | 4365 |
| φX174 | 2 | 2 | 5000 | 4985 | 3746 |
|  |  |  | 400 | 401 | 4143 |
| M13mp8 | 2 | 2 | 4900 | 4929 | 4074 |
|  |  |  | 2300 | 2300 | 6370 |
| pBR322 | 2 | 2 | 2500 | 2559 | 2535 |
|  |  |  | 1800 | 1804 | 4157 |
| pBR328 | 1 | 1 | 4900 | 4907 | 3037 |

The microorganism Kluyvera species 632 used for obtaining the enzyme grows anaerobically in Merck Standard I medium.

Kluyvera species 632 has been deposited at the "Deutsche Sammlung von Mikroorganismen, Mascheroder Weg 1 b, D-3300 Braunschweig, BRD" and bears accession number DSM 4196. The optimal growth temperature is 10° to 30° C. at pH 7.2-8.0. The cells are doubled after approximately 2 hours.

The enzyme is isolated and purified by the conventional mechanical and chemical methods for example high pressure dispersion, ultrasonics or enzymatic digestion.

In a preferred embodiment of the process according to the present invention, the cells are digested by a pressure of 5 bar. The cell mass is resuspended in Tris-HCl buffer pH 8.0 which contains protease inhibitors. The cells are then digested by a French press and precipitated by polymin and ammonium sulfate. The further purification of the supernatant containing the enzyme is preferably conducted by molecular sieve fractionation chromatography, over anion exchangers and over cation exchangers as well as by affinity chromatography. As molecular sieve material, there has proved to be useful the product which is commercially available under the designation Ultrogel AcA34 (LKB) as well as hydroxylapatit (Boehringer Mannheim GmbH).

As anion exchanger there is preferably used the product named DEAE Sephadex (Pharmacia). As affinity chromatography material there is preferably used heparin-Sepharose Cl-6B (Pharmacia). Other chromatography materials are also useful.

The following examples are given for the purpose of illustrating the present invention:

EXAMPLE 1

Kluyvera species 632 is allowed to grow at 30° C. for 20 hours and is harvested in the later logarithmic or stationary phase. As medium there is used Merck standard medium I. 30 g cell paste is resuspended in three volumes buffer A (50 mmol/l Tris-HCl, pH 8.0, 0.1 mmol/l EDTA, 7 mmol/l 2-mercaptoethanol) which contains protease inhibitors. Then the cells are digested twice by a French press at 23,000 lb/inch$^2$. Polymin (Polyethanolamine) is added and the precipitate formed is centrifuged and discarded. The supernatant is mixed with 60% (w/v) ammonium sulphate. The precipitate is isolated and dissolved in 15 ml buffer B (40 mmol/l Tris-HCl pH 8.0, 0.1 mmol/l EDTA, 7 mmol/l 2-mercaptoethanol, 10% (v/v) glycerin). The solution is fractionated on a sephacryl AcA34-chromatography column which was equilibrated by buffer B which contains 0.5 mmol/l NaCl. The active fraction is dialyzed against buffer B. Further purification is done on a hydroxylapatit column which was equilibrated with buffer B. For the elution a gradient of 0-1.0 mmol/l NaCl in buffer B was used. Ksp632I is found in the fraction between 0.4 and 0.6 mmol/l NaCl. The active fraction is dialysed against buffer B and chromatographed on a heparin sepharose Cl-6B-column which was equilibrated with buffer B. For elution a gradient of 0-1.0 mmol/l NaCl in buffer B is used. Ksp632I is found in the fraction between 0.4 and 0.6 mmol/l NaCl.

The active fractions are collected and dialyzed against storage buffer (20 mmol/l Tris-Hcl pH 8.0, 10 mmol/l 2-mercaptoethanol and 100 mmol/l NaCl, 0.1 mmol/l EDTA, 50% (v/v) glycerin).

EXAMPLE 2

Determination of activity

Definition of the enzyme units: 1 U Ksp632I cleaves 1 μg Lambda-DNA in 1 hour at 37° C. in 25 μl total volume.

Into a mixture of 12 μl incubation buffer, containing 66 mmol/l Tris acetate, pH 7.9/37° C., 20 mmol/l magnesium acetate, 132 mmol/l potassium acetate and 1 mmol/l dithiothreitol, 7 μl water and 5 μl lambda DNA (optical density: 4 OD/ml) as well as 1 μl Ksp632I-solution (1U/μl) are added. The solution is maintained at 37° C. for an hour, cooled on ice and mixed with 5 μl cold stop solution, containing 7 mmol/l urea, 20% (w/v) saccharose, 60 mmol/l EDTA and 0.01% (w/v) bromphenol blue. It is then separated electrophoretically on 1% agarose gel for 3-4 hours at 100 V. The bands obtained are identified in comparison with suitable DNA length standards.

It will be understood that the specification and examples are illustrative but not limitative of the present invention and that other embodiments within the spirit and scope of the invention will suggest themselves to those skilled in the art.

We claim:

1. A restriction endonuclease capable of recognizing and cleaving a DNA sequence at a position indicated by the arrows

5'-CTCTTCN ↓ NNN-N-3'

3'-GAGAAGN-NNN ↑ N-5'.

2. The restriction endonuclease of claim 1 wherein said endonuclease is characterized by an average temperature optimum at 37° C. and a pH optimum between 7.2 and 8.0.

3. A process for obtaining the restriction endonuclease of claim 1 comprising the steps of culturing Kluyvera species 632 DSM 4196 cells and recovering the restriction endonuclease from the cells.

4. The process of claim 3 comprising recovering the endonuclease from the cells of Kluyvera species 632 by digesting the cells to release an extract therefrom, mixing the extract released from the digested cells with polyethylenimine, separating insolubles from a supernatant, mixing the supernatant with ammonium sulphate in an amount of up to 60% saturation to form a precipitated fraction and recovering the precipitated fraction therefrom.

5. Process of claim 4 further comprising purifying the ammonium sulphate precipitated fraction by at least one process selected from the group consisting of molecular sieve fractionation, chromatography over a weakly basic anion exchanger, chromatography over a weakly acidic cation exchanger and affinity chromatography.

6. The process of claim 5 comprising purifying said ammonium sulphate precipitated fraction by affinity chromatography using carrier-fixed heparin.

7. Method for obtaining a DNA sequence having terminal nucleotide sequence indicated by the arrows:

5'CTCTTCN ↓ NNN-N-3'

3'GAGAAGN-NNN ↑ N-5' comprising contacting DNA with endonuclease Ksp632I under conditions favoring cleavage of DNA thereby and collecting cleaved DNA.

* * * * *